March 23, 1954 A. S. RITTER Plant Pat. 1,266
PHILODENDRON PLANT
Filed Sept. 7, 1951 2 Sheets-Sheet 1
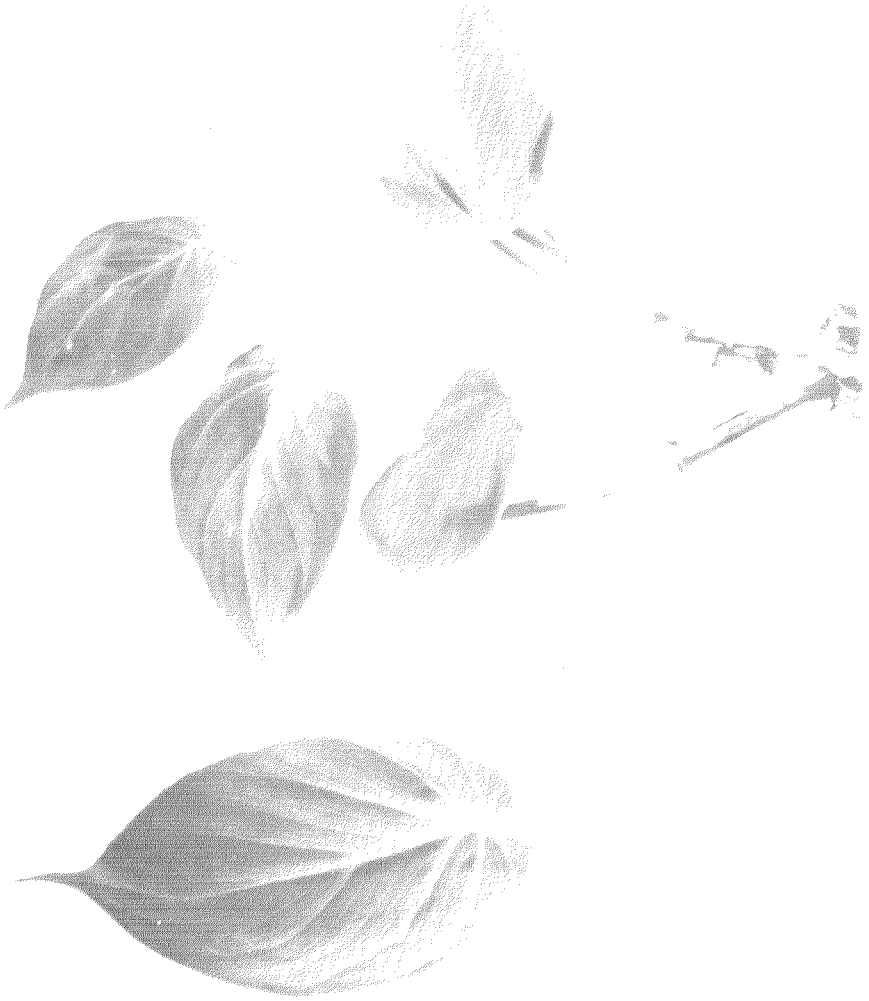
Inventor
Alexander S. Ritter
By Clarence A. O'Brien
and Harvey B. Jacobson
Attorneys

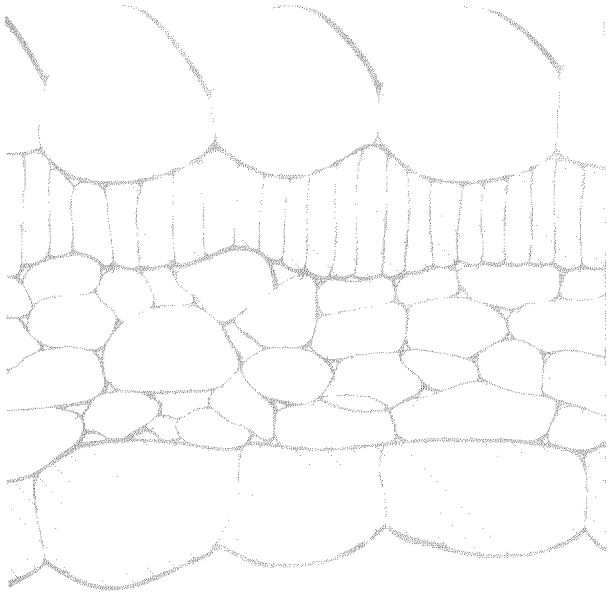
Alexander S. Ritter
Wm. Wm. York,
Oliver M. O'Brien
and Harvey B. Jackson
Attorneys Patented Mar. 23, 1954 Plant Pat. 1,266

UNITED STATES PATENT OFFICE 1,266

PHILODENDRON PLANT

Alexander S. Ritter, Brielle, N. J.

Application September 7, 1951, Serial No. 245,464

1 Claim. (Cl. 47—59)

The present variety of philodendron plant originated as a sport of *Philodendron cordatum* discovered in the course of breeding efforts carried on by me since 1946 in my greenhouses in Brielle, New Jersey. Over fifty thousand plants of this new variety have been propagated, some being in the fortieth generation, and the novel characteristics have been maintained.

Asexual propagation is by cuttings in my greenhouses in Brielle, New Jersey. My development of the variety has been as an indoor plant of ornamental appearance. The vine is sturdy with rather short stemjoints having a compact internode spacing and dense foliage, the leaf being heart-shaped.

The drawings disclose a photographic illustration of the philodendron plant and a magnified cross-sectional view of a leaf thereof.

The leaves are characterized as green in color. The veinings are pronounced, being a somewhat grey-white shade lighter in color tone than the rest of the leaf surface and forming deep depressions in the surface of the leaf as shown in the illustration. The border of the leaf is characterized by a ridge-like edge of the same lighter shade as the veining which can also be seen in the photographic illustration in the drawings.

The leaves are also characterized by a papillate development of their upper epidermis, as is illustrated by the cross-sectional view in the drawings shown at a magnification of 375 times the true size of the leaf tissue. The papillae, or pimple-like cells of the upper epidermis are approximately .003" wide at their base, project approximately .002" above the normal surface of the leaf, and exist in the density of approximately one million units per square inch. These papillae give the upper surface of the leaf a velvet-like nap or texture and scatter light falling thereon so as to give the leaf a velvet-like appearance.

Undersurfaces of the leaves are smooth in texture and somewhat lighter in shade than the top with a tendency to a slight reddish tinge along the edge of the leaf before maturity.

The general shape and size of the leaf corresponds generally with the common well known varieties of *Philodendron cordatum*. Extensive observation over a period of time of this variety with the common variety shows that the velvety appearance is a distinguishing feature which feature runs true to form through succeeding generations.

I claim:

A new and distinct variety of philodendron plant, substantially as described and illustrated, characterized by leaves having deep veining, a relatively smooth undersurface and an upper epidermis consisting of juxtaposed papillae which give the upper surface of the leaf a velvet-like nap or texture and scatter light falling thereon so as to give the leaf a velvet-like appearance.

ALEXANDER S. RITTER.

References Cited in the file of this patent

UNITED STATES PATENTS

| Number | Name | Date |
|---|---|---|
| Pl. Pt. 1,046 | Hahn | Oct. 30, 1951 |